United States Patent
Liang et al.

(10) Patent No.: US 10,307,393 B2
(45) Date of Patent: Jun. 4, 2019

(54) APPLICATION OF NARINGENIN AND NARINGIN IN TUMOR RADIOTHERAPY

(71) Applicant: INSTITUTE OF BIOPHYSICS CHINESE ACADEMY OF SCIENCES, Beijing (CN)

(72) Inventors: Wei Liang, Beijing (CN); Chun Ling Zhang, Beijing (CN); Wen Feng Zeng, Beijing (CN); Chao Zhang, Beijing (CN); Luo Yang Wang, Beijing (CN)

(73) Assignees: INSTITUTE OF BIOPHYSICS CHINESE ACADEMY OF SCIENCES, Beijing (CN); TOPFOND PHARMACEUTICAL CO., LTD., Zhumadian (CN)

( * ) Notice: Subject to any disclaimer, the term of this patent is extended or adjusted under 35 U.S.C. 154(b) by 0 days.

(21) Appl. No.: 15/743,288

(22) PCT Filed: Aug. 25, 2016

(86) PCT No.: PCT/CN2016/096711
§ 371 (c)(1),
(2) Date: Jan. 10, 2018

(87) PCT Pub. No.: WO2017/008769
PCT Pub. Date: Jan. 19, 2017

(65) Prior Publication Data
US 2018/0200223 A1 Jul. 19, 2018

(30) Foreign Application Priority Data

Jul. 10, 2015 (CN) .......................... 2015 1 0404716

(51) Int. Cl.
| | | |
|---|---|---|
| *A61K 31/353* | (2006.01) | |
| *A61K 31/352* | (2006.01) | |
| *A61P 35/00* | (2006.01) | |
| *A61K 45/06* | (2006.01) | |
| *A61K 31/7048* | (2006.01) | |
| *A61K 41/00* | (2006.01) | |
| *A61N 5/10* | (2006.01) | |

(52) U.S. Cl.
CPC .......... *A61K 31/353* (2013.01); *A61K 31/352* (2013.01); *A61K 31/7048* (2013.01); *A61K 41/0038* (2013.01); *A61K 45/06* (2013.01); *A61P 35/00* (2018.01); *A61N 5/10* (2013.01)

(58) Field of Classification Search
CPC ..... A61K 31/353; A61K 31/352; A61P 35/00; A61N 5/10
See application file for complete search history.

(56) References Cited

U.S. PATENT DOCUMENTS

2003/0118536 A1* 6/2003 Rosenbloom ............ A61K 8/42
424/70.1

FOREIGN PATENT DOCUMENTS

| CN | 101322700 A | 12/2008 |
|---|---|---|
| CN | 101322700 B | 8/2010 |
| CN | 102302483 A | 1/2012 |
| CN | 104940932 A | 9/2015 |

OTHER PUBLICATIONS

Wang et al, Asian Pacific Journal of Cancer Prevention, vol. 13, 6441-6446. (Year: 2012).*
Pan et al, Food Funct., 2010, 1, 15-31. (Year: 2010).*
Hogle WP, The State of the Art in Radiation Therapy, Semin Oncol Nurs, Nov. 2006, pp. 212-220, vol. 22, No. 4.
Van Den Brenk, H.A et al, Potentiating effect of prior local irradiation of the lungs on pulmonary metastases, Br J Radiol, 47(558): pp. 332-336, (1974).
Muruve DA et al, The inflammasome recognizes cytosolic microbial and host DNA and triggers an innate immune response, Nature, Mar. 6, 2008, 452(7183):pp. 103-107.
Lerman, O.Z., et al., Low-dose radiation augments vasculogenesis signaling through HIF-1-dependent and- independent SDF-1 induction, Blood, Nov. 4, 2010, vol. 116, No. 18, pp. 3669-3676.
Du, R., et al., HIF1α Induces the Recruitment of Bone Marrow-Derived Vascular Modulatory Cells to Regulate Tumor Angiogenesis and Invasion, Cancer Cell, 13(3):pp. 206-220, (2008).
Sime, P.J., et al., Transfer of Tumor Necrosis Factor-α to Rat Lung Induces Severe Pulmonary Inflammation and Patchy Interstitial Fibrogenesis with Induction of Transforming Growth Factor-β1 and Myofibroblasts, Am J Pathol, Sep. 1998, vol. 153, No. 3, pp. 825-832.
Laura S., et al., Complement Is a Central Mediator of Radiotherapy-Induced Tumor-Specific Immunity and Clinical Response, Immunity, 42(4), pp. 767-777, (2015).
Sakamoto K, et al., Reduced effect of irradiation on normal and malignant cells irradiated in vivo in mice pretreated with vitamin E, Br J Radiol, 46(547): 538-540, (1973).
Prasad K.N., et al., Effect of individual and multiple antioxidant vitamins on growth and morphology of human nontumorigenic and tumorigenic parotid acinar cells in culture, Nutr Cancer 26(1): 11-19, (1996).
El Touny L.H., et al., Identification of a Biphasic Role for Genistein in the Regulation of Prostate Cancer Growth and Metastasis, Cancer Res. 69(8):pp. 395-703, (2009).
Tunon M.J., et al., Potential of Flavonoids as Anti-inflammatory Agents: Modulation of Pro-Inflammatory Gene Expression and Signal Transduction Pathways, Current Drug Metabolism, 10, pp. 256-271, (2009).

(Continued)

*Primary Examiner* — Sudhakar Katakam
(74) *Attorney, Agent, or Firm* — Gokalp Bayramoglu

(57) ABSTRACT

The present invention provides applications of a small molecular flavonoid compound in preparing a medication for sensitizing/synergizing tumor radiation therapy as well as reducing radioactive damage. The small molecular flavonoid compound can be naringenin, hesperetin, luteolin and apigenin, etc. The medication contains a small molecular flavonoid compound and a plurality of conventional pharmaceutical additives; wherein the small molecular flavonoid compound is an active ingredient.

10 Claims, 5 Drawing Sheets

(56) References Cited

OTHER PUBLICATIONS

Du GJ, et al., Naringenin: A Potential Immunomodulator for Inhibiting Lung Fibrosis and Metastasis, Cancer Res 69(7): pp. 3205-3212, (2009).
Lou CJ, et al, Naringenin Decreases Invasiveness and Metastasis by Inhibiting TGF-β-Induced Epithelial to Mesenchymal Transition in Pancreatic Cancer Cells, PLOS one, 7(12), e50956, (2012).

* cited by examiner

APPLICATION OF NARINGENIN AND NARINGIN IN TUMOR RADIOTHERAPY

CROSS REFERENCE TO RELATED APPLICATIONS

This application is the national phase entry of International Application No. PCT/CN2016/096711, filed on Aug. 25, 2016, which is based upon and claims priority to Chinese Patent Application No. CN201510404716.2, filed on Jul. 10, 2015, the entire contents of which are incorporated herein by reference.

TECHNICAL FIELD

The present invention relates to the technical field of medical products, in particular to an application of naringenin and naringin in tumor radiation therapy, in particular to an application of preparing a medication for sensitizing tumor radiotherapy as well as reducing radiation-induced toxicity.

BACKGROUND

Radiotherapy is an indispensable strategy for cancer treatment. About 60-70% of patients with malignancies receive radiation therapy which can cure many tumors and the cure rates of radiotherapy on early tongue cancer, nasopharynx, laryngeal cancer, esophageal cancer and cervical cancer are about 90% [Hogle W P, Semin Oncol Nurs, 22 (4): 212-220, (2006)]. However, when killing the tumor, radiotherapy will cause off-target effect on normal tissue (including non-cancerous tissue inside the radiation shield and distant tissues such as bone marrow), which is the major reason limiting the efficacy of radiotherapy. Although measures including the equipment updating to improve radiotherapy accuracy, cooperative usage of radiosensitizers and combination with chemotherapy have been tried, the results remain unsatisfactory. The main question turns out to be the incapability of normal tissues to tolerate radiation-induced toxicity, which prevents higher dose of radiotherapy in clinical applications. Radiation-induced lung injury is the most common clinical complications post-radiotherapy. In severe cases, it may endanger the patient's life, especially who suffer from lung tumor, esophageal tumor, breast tumor and mediastinal tumor.

Radiation-induced lung injury (RILI) consists of radiation pneumonitis in the early stage and radio-pulmonary fibrosis in the late stage. Such injury not only undermines the control of tumor, but also seriously affects the quality of life of the patients. Respiratory failure is one of the leading causes of death in RILI. In addition, local hypoxia, inflammatory response, angiogenesis, local microenvironmental changes and immunosuppression caused by RILI will promote tumor recurrence, invasion and metastasis [van den Brenk, H A et al, Br J Radiol, 47 (558): p. 332-336, (1974)]. Thus, it is particularly important to manage RILI in clinic, but the lack of effective drug leading to empirical use of high-dose glucocorticoid and anti-inflammatory drugs. These measures not only fail to improve the therapeutic effect of radiotherapy, but also cause many side effects, such as immunosuppression after long-term high-dose usage of glucocorticoids. Additionally, pulmonary immunosuppressive microenvironment spurs the risk of tumor recurrence and metastasis. It has been an urgency for tumor radiotherapy to discover a drug that can both prevent/treat RILI and reduce tumor recurrence or metastasis.

It is generally accepted that the tumor-killing effect of radiotherapy is due to radiation-induced DNA damage and the production of free radicals inside tumor cells [Muruve D A et al, Nature, 452 (7183): 103-107, (2008)]. Subsequently, DNA fragments and reactive oxygen species (ROS) trigger the inflammation, during which the activated macrophages synthesize and secrete a large amount of inflammatory cytokines, such as TNF-$\alpha$, IL-1$\beta$, IL-8, etc. High levels of TNF-$\alpha$ and fibronectin together can cause the initial acute pneumonitis, which can also promote the proliferation of fibroblasts and stimulate fibroblasts to secrete excess collagen at the same time. Radiation-induced oxidative damage in the pulmonary capillary endothelial cells, including DNA breakage, cell death, and the increase of ROS/RNS, causes the accumulation, transcription and up-regulated activity of HIF in tumor cells [Lerman, O Z, et al., Blood, 116 (18): 3669-3676, (2010)]. Under hypoxia, vascular endothelial cells (ECs) produce a large amount of chemokine SDF, which binds to CXCR4 and recruits BMDCs to inflammatory lesions [Du, R., et al., Cancer Cell, 13 (3): 206-220, (2008)]. A big body of studies have shown that BMDCs are crucial for the formation and growth of tumor neovascularization. The changes of the microenvironment provide a favorable condition for tumor recurrence and metastasis.

The sustained and persistent immune response after the radiotherapy will cause chronic inflammation, which will then initiate the process of tissue remodeling and repair. The repair of normal tissue and infiltration of inflammatory cells promote the transformation of myofibroblasts and the secretion of transforming growth factor (TGF-$\beta$) and connective tissue growth factor (CTGF). Wherein TGF-$\beta$ is a multifunctional cytokine involved in the regulation of cell proliferation, differentiation and extracellular matrix secretion, which is the most important cytokine in the pathogenesis of fibrosis [Sime, P J, et al., Am J Pathol, 153 (3): 825-832, (1998).]. However, the tissue repair process after radiotherapy is distinct from the repair process of normal tissue. Radiotherapy causes the dysfunction of vascular endothelial cells, followed by vascular lesions formation, and hypoxia-induced irreversible tissue proliferation, which finally results in radiation-induced fibrosis in the late stage.

Clinical studies have demonstrated that despite typical glucocorticoids such as dexamethasone, can effectively alleviate early radiation-induced pneumonia due to the immunosuppressive property, they potentially ablate the efficacy of radiotherapy and may worsen radiation-induced pulmonary fibrosis [Laura S., et al., Immunity, 42 (4), 767-777, (2015)]. Other studies have shown that a diet containing flavonoids have significant antioxidant effect. Polyphenols, vitamin E, etc. also have significant radioprotective effects. However, they are finally abandoned, due to the fact that the protective effects of these antioxidants on radiotherapy often results in the counteraction against radiotherapy [Sakamoto K, et al., Br J Radiol. 46 (547): 538-540, (1973)] or tumor recurrence. [Prasad K N, et al., Nutr Cancer.—19, (1996)].

The existing drugs for the prevention and treatment of RILI have protective effects, but they tend to ablate the therapeutic effect of radiotherapy, which leaves a dilemma to clinic. Therefore, a drug which can prevent RILI without affecting the efficacy of radiotherapy is urgently needed in clinic.

Flavonoids (the general structural formula shown in Formula 1) have antioxidant and free radical scavenging effects. Such compounds can terminate the free radical chain reaction by reacting phenolic hydroxyl groups with free radicals to generate more stable semicarbazide-type free radicals. Domestic and foreign scholars have found that soy isoflavones in flavonoids, such as genistein, have significant antioxidant and free radical scavenging effects and have a certain protective effect on RILL But genistein promotes metastasis in some hormone-related tumors. This study found many limitations in clinical applications of genistein in the future [El Touny L H, et al., Cancer Res. 69 (8): 3695-703, (2009)].

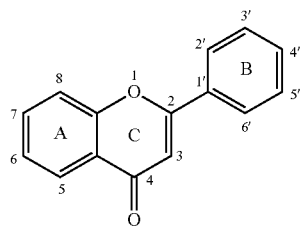

Formula 1: the general structural formula of flavonoids.

Naringin (the structure formula shown in Formula 2, naringin), also known as naringoside and hesperetin, with a molecular formula of $C_{27}H_{32}O_{14}$ and a molecular weight of 580.53, mainly exists in the peel and pulp of Rutaceae plants including grapefruit, mandarin orange and orange. Naringin is also the main active ingredient of Chinese herbal *rhzizoma drynariae, citrus aurantium, fructus aurantii* and *exocarpium citri rubrum*.

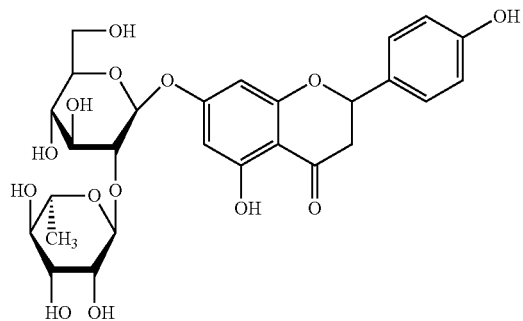

Formula 2: the general structural formula of naringin.

Naringenin (naringenin, the structure formula shown in Formula 3) is the aglycone of naringin, and also the structure part of the naringin exerting its pharmacological effects. The naringenin has a molecular formula of $C_{15}H_{12}O_5$ and a molecular weight of 272.25, with antibacterial, anti-inflammatory, spasmolytic and diuretic effects [12-14]. The structural formula of flavonoid and naringenin and naringin is as follows:

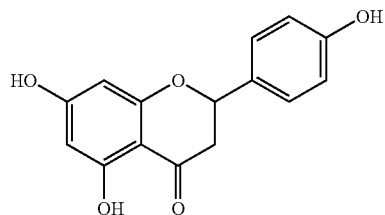 [SMILES: O=C1CC(c2ccc(O)cc2)Oc2cc(O)cc(O)c21]

Formula 3: the general structural formula of naringenin.
B ring of the flavonoid is the main active site responsible for the antioxidant and free radicals scavenging effects. When there are ortho-hydroxyls in the ring, the antioxidant capacity will be greatly enhanced. The 2, 3 double-bond is preferable to the formation of a more stable free radical after the B ring loses electrons. The 4-carbonyl can form a hydrogen bond with the ortho-hydroxyl to make the free radical intermediates more stable. The 3,5-hydroxyl belongs to the synergizing phenolic hydroxyl. Thus, naringenin and naringin do not have significant antioxidant effects as soy isoflavones do [M. J, et al., Current Drug Metabolism, 10, 256-271, (2009)].

Based on systematic research, we found that naringenin and naringin exert the anti-fibrosis and anti-metastasis effects by regulating the secretion of TGF-β [CN 101322700 B; Du G J, et al., Cancer Res 69 (7): Lou C J, et al, PLOS one, 7 (12), e50956, (2012)]. Moreover, naringenin and naringin regulate the release of immune-related inflammatory cytokines to prevent radiation-initiated tumor recurrence and metastasis without affecting the therapeutic effect of radiotherapy on tumor.

SUMMARY OF THE INVENTION

The present invention relates to applications of a small molecular flavonoid compound in sensitizing/synergizing tumor radiotherapy as well as reducing radiation-induced toxicity.

The present invention further relates to an application of a small molecular flavonoid compound in preparing a medication for sensitizing/synergizing tumor radiotherapy as well as reducing radiation-induced toxicity.

The present invention further relates to an application of a small molecular flavonoid compound in regulating the release of a plurality of immune-related cytokines thereof to sensitize/synergize tumor radiotherapy as well as reducing radiation-induced toxicity.

The present invention further relates to an application of a small molecular flavonoid compound in preparing a pharmaceutical formulation regulating the release of a plurality of immune-related cytokines.

The small molecular flavonoid compound is naringenin, hesperetin, luteolin, apigenin, etc., preferably naringenin or naringin.

The tumor radiotherapy is a clinically applicable radiation therapy method, for example:
(1) external or internal radiation therapy;
(2) stereotactic radiation therapy;
(3) direct ionizing radiation therapy or indirect ionizing radiation therapy;
(4) radiation therapy using X-ray therapy apparatus, medical accelerator or radioactive nuclide.

The tumor is preferably thoracic tumor, such as lung tumor, esophageal tumor, breast tumor and mediastinal tumor.

The inflammatory cytokines include but are not limited to interleukin 6 (IL-6), interleukin 1β (IL-1β), TNF-α, TGF-β and IFN-γ.

The radiation-induced toxicity consists of tissue inflammation or tissue fibrosis caused by radiation.

The radiation-induced toxicity is preferably radiation-induced lung injury including radiation pneumonitis in the early stage of radiotherapy and radiation pulmonary fibrosis in the late stage of radiotherapy.

The present invention further relates to a pharmaceutical composition or a pharmaceutical preparation for sensitizing/synergizing tumor radiotherapy and reducing radiation-induced toxicity prepared from a small molecular flavonoid compound as an active ingredient. The pharmaceutical composition or the pharmaceutical preparation includes a small molecular flavonoid compound and a plurality of conventional pharmaceutical additives. The plurality of conventional pharmaceutical additives includes an excipient, a disintegrant, a supporter, a sustained-release ingredient, etc. The pharmaceutical preparation is a conventional preparation including tablet, capsule, injection, and powder.

DETAILED DESCRIPTION OF THE INVENTION

Figure 1:
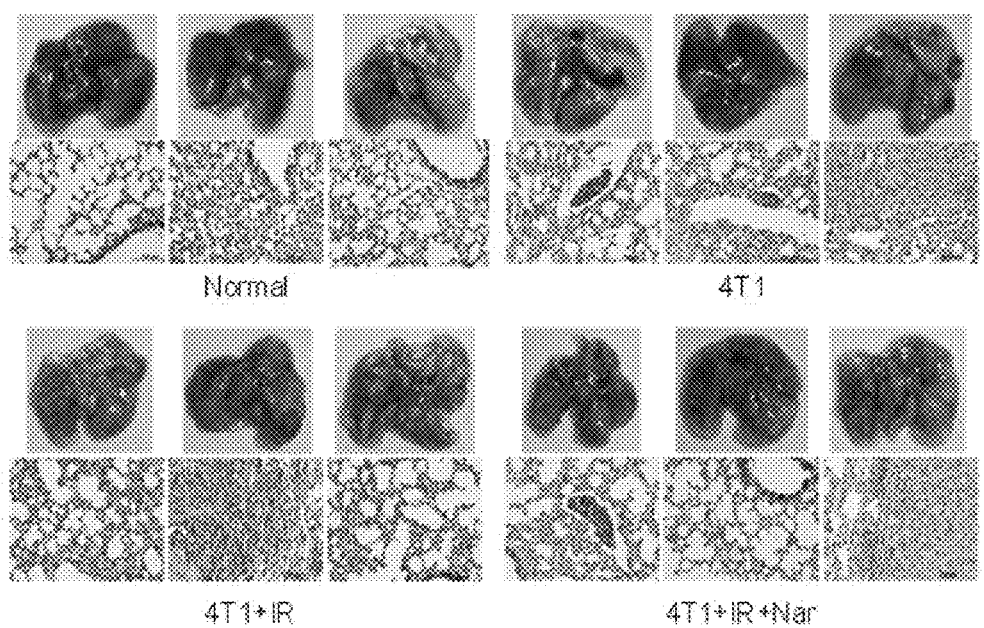
FIG. 1 Naringenin ameliorates the radiation-induced lung injury in 4T1 breast tumor bearing mice with lung metastasis after radiotherapy.

Embodiment 1 Naringenin Ameliorates the Radiation-Induced Lung Injury, Modulates the Immune-Related Cytokines and Prolongs the Survival in 4T1 Breast Tumor Bearing Mice with Lung Metastasis after Radiotherapy Cell Culture and Animal Model Establishment:

(1) Resuscitation and culture of 4T1 cells: Cell culture hood need to be sterilized by UV for 30 min before resuscitating the 4T1 cells. Equilibrate the RPMI 1640 culture medium (containing 10% fetal bovine serum) to room temperature for further application. The cryovial containing tumor cells are taken from liquid nitrogen storage and immediately put into a 37° C. water bath, shaking quickly until the cells are completely dissolved. Transfer the cells into a cell culture flask with 10-15 ml medium to suspend the sedimentary cells. After adjusting the concentration of the cells, culture the cells in an incubator with a saturated humidified atmosphere containing 5% (v/v) $CO_2$ at 37° C. Replace fresh medium every day during. Digest the cells by 0.25% trypsin when the convergence of the cells reaches 90%, and then subculture the cells at a ratio of 1:3. On the day of experiment, we collect the cells by digesting the cells with 0.25% trypsin, then neutralize the trypsin with RPMI 1640 with 10% fetal bovine serum. Centrifuge the cells at 800 rpm, and then resuspend the cells in sterile PBS. After counting the density of cells, adjust the cells to $1 \times 10^5$/ml for tumor cells inoculation.

(2) 4T1 cells are mixed well before inoculation. Pipet 0.3 ml of cells by a 1 ml sterile syringe, and inject 0.1 ml of cells per mouse (namely $1 \times 10^4$ 4 T1 cells per mouse).

Experimental Program 1: Naringenin Ameliorates the Radiation-Induced Lung Injury in 4T1 Breast Tumor Bearing Mice with Lung Metastasis and Regulates the Immune-Related Cytokines after Radiotherapy (1) 4T1 murine breast tumor cell line was used to inoculate the tail vein of Balb/C mice to form lung metastatic tumors. $1 \times 10^4$ 4 T1 cells were intravenously injected into the tail vein per mouse, and 10-15 days later nodules would develop in lung.

(2) Set the day of inoculation as day 0. 200 mg/kg naringenin (Nar) (suspended in 1% CMC-Na) was administered orally to the mice at day 12 day after inoculation, namely 3 days before irradiation on the lungs. The mice received a 12 Gy of γ-ray irradiation once at day 14 after inoculation and keep naringenin administration. A part of the mice in each group were sacrificed at day 28 after inoculation and the blood, lung tissues were collected while the lungs were weighed. The tumor nodules in the lungs were observed under the condition of without destroying the integrity of lung tissues. Serum were separated and assayed for cytokines such as IL-6, IL-1β, IFN-γ, etc. The lung tissues collected at day 28 after inoculation were used for biopsy and the observation of lung injury as well as inflammatory cells infiltration. The rest animals were used for survival observation.

(3) Grouping method for mice

The mice in this experiment are separated into 4 groups as follows:
1) Normal control group (Normal)
2) 4T1 tumor-bearing mice without irradiation group (4T1)
3) 4T1 tumor-bearing mice receiving lung irradiation without naringenin administration group (4T1+IR)
4) 4T1 tumor-bearing mice receiving lung irradiation with naringenin administration group (4T1+IR+Nar)

3 groups of mice were inoculated with 4T1 tumor cells. Each group contains 12 mice with half male and half female which were fed in separate cages, and each cage contains 6 mice.

As shown in FIG. 1, naringenin administration decreased the number of tumor nodules in lungs compared to 4T1 group and 4T1+IR group. Meanwhile, the pathological analysis showed that severe lung damage and fibrosis in 4T1+IR group, and the lung injury and fibrosis were markedly alleviated in 4T1+IR+Nar group.

Figure 3:
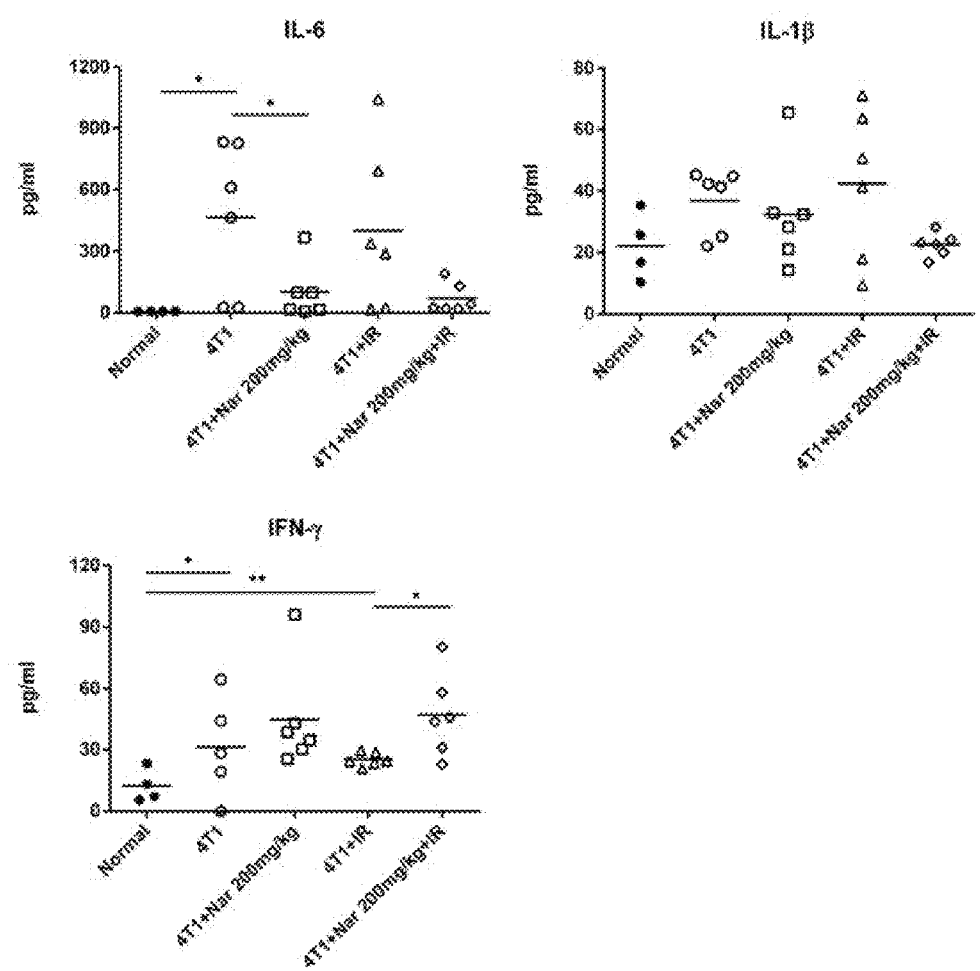
FIG. 3 Effect of naringenin on immune-related cytokines induced by radiotherapy on mice bearing 4T1 breast tumor with lung metastasis.

As shown in FIG. 3, upon naringenin treatment the levels of cytokines including IL-6, IL-1β and IFN-γ were significantly changed as compared to those in the 4T1+IR group.

Experimental Program 2: Naringenin Prolongs the Survival of Mice Bearing 4T1 Breast Tumor with Lung Metastasis after Radiotherapy.

(1) 4T1 murine breast tumor cell line was intravenously injected to form lung metastatic tumors in Balb/c mice. Lung metastatic nodules would develop about 10-15 days after $1 \times 10^4$ 4 T1 cells were inoculated.

(2) Set the day of inoculation as day 0, at day 12 after inoculation, different doses of naringenin (Nar), namely 50, 100 and 200 mg/kg (suspended in 1% CMC-Na), were administered orally. The mice received γ-ray irradiation (8 Gy×2 f) at day 14 and day 15 after inoculation. Wherein the naringenin was administered orally in the $4^{th}$, $5^{th}$ and $6^{th}$ groups, the positive medicine dexamethasone (0.25 mg/kg) plus cefixime (200 mg/kg) were administered orally in the 7th group. The administration of either naringenin or dexamethasone plus cefixime continued until the mice started to die, and the survivals were observed and recorded.

(3) Grouping method for mice

The mice in this experiment are divided into 7 groups as follows:
1) Normal control group (Normal)
2) 4T1 tumor-bearing mice without irradiation group (4T1)

3) 4T1 tumor-bearing mice receiving lung irradiation without naringenin administration group (4T1+IR)
4) 4T1 tumor-bearing mice receiving lung irradiation with 50 mg/kg naringenin administration group (4T1+IR+Nar 50 mg/kg)
5) 4T1 tumor-bearing mice receiving lung irradiation with 100 mg/kg naringenin administration group (4T1+IR+Nar 100 mg/kg)
6) 4T1 tumor-bearing mice receiving lung irradiation with 200 mg/kg naringenin administration group (4T1+IR+Nar 200 mg/kg)
7) 4T1 tumor-bearing mice receiving lung irradiation with dexamethasone (DXM) plus cefixime (CXL) administration group (4T1+IR+DXM+CXL)

6 groups of mice were inoculated with 4T1 tumor cells. Each group contains 12 mice with half male and half female, which were fed in separate cages, and each cage contains 6 mice.

Figure 2:
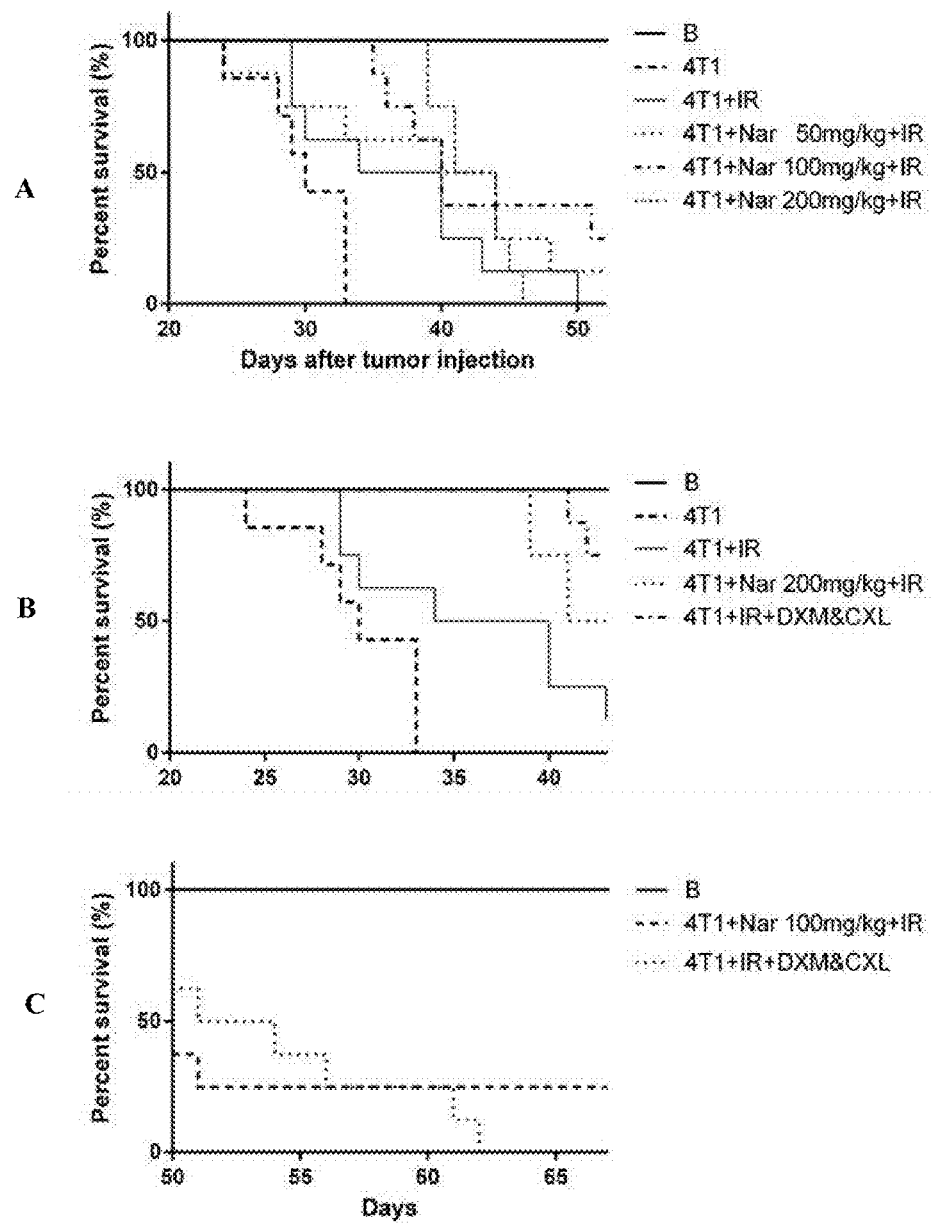
FIG. 2 Naringenin prolongs the survival of mice bearing 4T1 breast tumor with lung metastasis after radiotherapy.

As shown in FIG. 2, compared with 4T1+IR group, all 3 doses of naringenin significantly prolonged the survival of tumor-bearing mice. Especially, 100 mg/kg naringenin exerted the highest sensitizing/synergizing effect combined with radiotherapy. Furthermore, even when compared with the positive drugs (DXM+CXL), 100 mg/kg naringenin still showed an improvement in the survival of tumor-bearing mice.

Embodiment 2. Synergistic Effect of Naringenin on Radiotherapy Efficacy and Survival in Mice Bearing LLC Lung Cancer Experimental Design:
(1) LLC murine lung cancer cell line was used to intravenously inoculate the C57B6/L mice to form lung metastatic tumors. About 24 days after $5\times10^5$ LLC cells were inoculated, nodules in the lung would develop.
(2) The mice were divided into 4 groups, and each group contains 10 mice. The grouping methods are as followed:
 1) Normal control group (Normal);
 2) LLC tumor-bearing mice without irradiation group (LLC);
 3) LLC tumor-bearing mice receiving lung irradiation without naringenin administration group (LLC+IR);
 4) LLC tumor-bearing mice receiving lung irradiation with naringenin (Nar) administration group (LLC+IR+Nar); Set the day of inoculation as day 0.
(6) 100 mg/kg naringenin (Nar) (suspended in 1% CMC-Na) was administered orally to each of the mice in LLC+IR+Nar group at day 12 after inoculation (namely 3 days before lung irradiation);
(7) The mice received γ-ray irradiation with a dose of 12 Gy per mouse per time at day 14 after inoculation;
(8) Continue to orally administrate 100 mg/kg naringenin (Nar) (suspended in 1% CMC-Na) to each of the mice in LLC+IR+Nar group at day 15 day after inoculation (namely 1 day after lung irradiation);
(9) At day 21 after inoculation, 5 animals in each group were randomly selected for sample collection. After dissection, the blood and lung tissues were collected, and the lungs were weighed. Then the number of tumor nodules in the lungs were counted without destroying the complete structure of lung tissues.
(10) At day 37 after inoculation, the remaining animals in each group were sacrificed and dissected. The blood and lung tissues were collected, and the lungs were weighed. Then the number of tumor nodules in the lungs were counted without destroying the complete structure of lung tissues.

Serum was separated and assayed for inflammatory cytokines such as IL-6, IL-113, IFN-γ, etc. The lung tissues were used for biopsy and the observation of lung injury and inflammatory cells infiltration. The immunohistochemistry was employed to detect lung DNA fragments (to investigate radiation-induced apoptosis), and the expression of collagen (to investigate lung fibrosis), etc. In order to gain a clear and comprehensive observation on the changes around blood vessels and bronchioles in lung sections, the left lungs were sliced vertically while the right lungs were sliced longitudinally.

Experimental Design
(2) Cell Culture and Resuscitation:
Cell culture hood need to be sterilized by UV for 30 min before resuscitating the LLC cells. Equilibrate the DMEM culture medium (containing streptomycin & penicillin and 10% fetal bovine serum, from PAA) to room temperature for further application. The cryovial containing tumor cells are taken from liquid nitrogen storage and immediately put into the 37° C. water bath, shaking quickly until the cells are completely dissolved. Transfer the cells into a cell culture flask with 10-15 ml medium to suspend the sedimentary cells. After adjusting the concentration of the cells, culture the cells in an incubator with a saturated humidified atmosphere containing 5% (v/v) $CO_2$ at 37° C. Replace fresh medium every day during. Digest the cells by 0.05% trypsin when the convergence of the cells reaches 90%, and then subculture the cells at a ratio of 1:3. According to the growth state of LLC cells, the cells were used for tumor inoculation after two passages.

On the day of experiment, we collect the cells by digesting the cells with 0.05% trypsin, then neutralize the trypsin with DMEM with 10% fetal bovine serum. Centrifuge the cells at 900 rpm for 5 minutes, and then resuspend the cells in sterile PBS. After counting the density of cells, adjust the cells to $50\times10^5$/ml for tumor cells inoculation.

(2) Tumor Inoculation
The LLC cells ($50\times10^5$/ml suspended in sterile PBS) were placed on ice in a cell culture hood which had been sterilized by UV for 30 min. The C57 mice grouped on the previous day were transferred to the experiment room. The mice were divided into 12 groups with 5 mice in each group. Mix the cells well before inoculation, and take 0.3 ml cell suspension by a 1 ml sterile syringe to inject 3 mice (0.1 ml per mouse). Then, take 0.2 ml by a 1 ml sterile syringe to inject 2 mice (0.1 ml per mouse).

Figure 4:
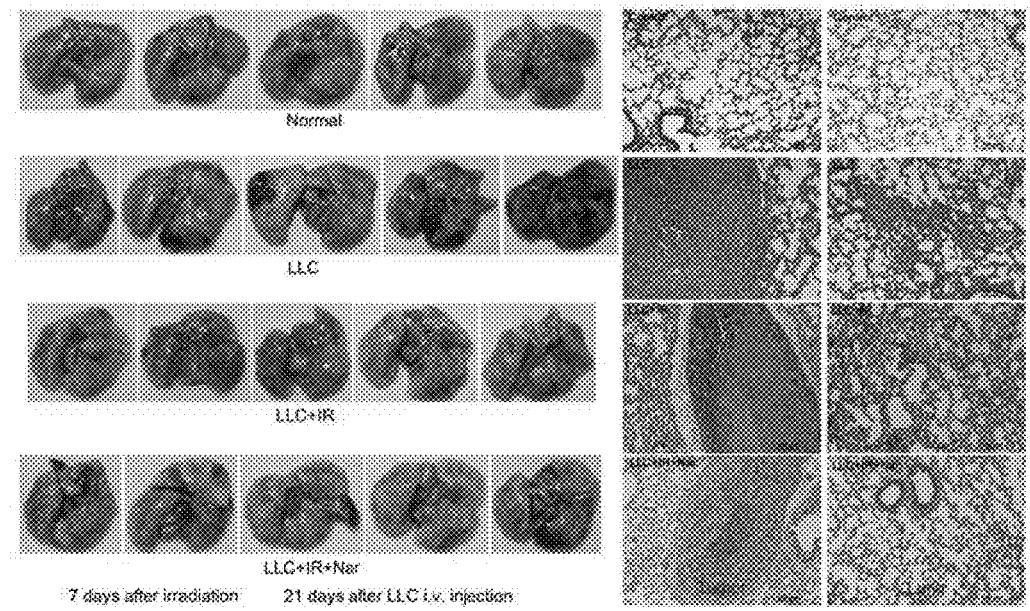
FIG. 4 Synergistic effect of naringenin on radiotherapy on mice bearing LLC lung tumor.
Figure 5:
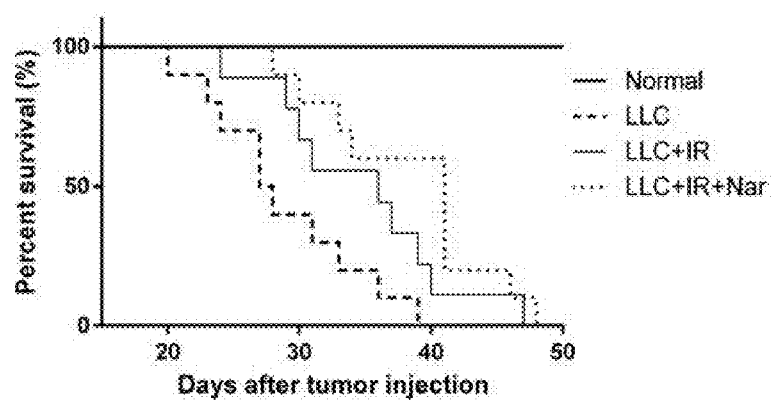
FIG. 5 Naringenin prolongs the survival of mice bearing LLC lung tumor after radiotherapy.

As shown in FIG. 4 and FIG. 5, naringenin administration significantly decreased the number of tumor nodules in lungs compared to those in LLC and LLC+IR group. Meanwhile, the pathological analysis showed that severe damage and fibrosis in lung tissues of LLC+IR group. And the lung injury in LLC+IR+Nar group was significantly alleviated.

Embodiment 3. Naringenin Reduces the Release of DNA Fragment-Induced Inflammatory Cytokine IL-1β

Experimental Design:
4% Brewer thioglycollate medium (1.5 ml/mouse) was intraperitoneally injected. Four days later, washing the abdominal cavity of these mice with serum-free medium (DMEM) (10 ml/mouse). The lavage fluids were collected and centrifuged at 1300 rpm for 5 minutes. The cell pellet was resuspended and seeded into a 24-well plate at the concentration of $2\times10^6$ cells/well. Two hours later, the non-adherent cells were carefully removed and the remaining adherent cells are primary peritoneal macrophages.

Identification: Macrophage surface marker F4/80 was detected by flow cytometry using PE-labelled anti-F4/80 antibody (ebioscience). The result shows that more than 90% of adherent cells were macrophages.

Sample treatment: The macrophages were pretreated with 100 μM naringenin (Nar) for 2 h, and then were stimulated with DNA fragments (100 ng/mL) for 24h. The supernatants were collected and the concentration of inflammatory cytokine IL-1β (pg/mL) in the supernatant was measured by ELISA.

Figure 6:
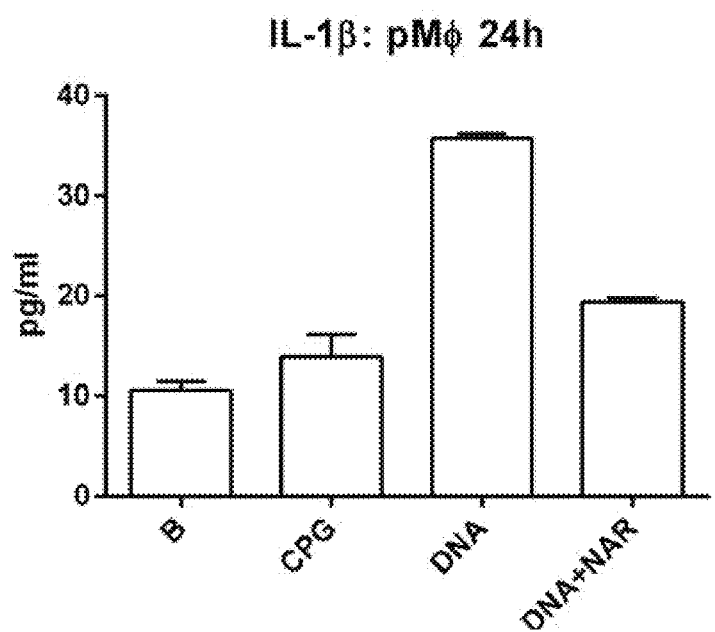
FIG. 6 Naringenin reduces the release of DNA fragment-induced inflammatory cytokine IL-1β.

The results are shown in FIG. 6, Naringenin significantly reduces the release of inflammatory cytokine IL-1β.

Embodiment 4: Antioxidative Effect of Flavonoids Including Naringenin

The total antioxidant capacity of several flavonoids was detected by the total antioxidant capacity test kit (FRAP method). The principle of the FRAP method is that the antioxidant can reduce ferric-tripyridyltriazine ($Fe^{3+}$-TPTZ) to produce a blue $Fe^{2+}$-TPTZ under an acidic condition. Measuring the blue $Fe^{2+}$-TPTZ at a wavelength of 593 nm to access the antioxidant capacity of the sample. Since the reaction is carried out under an acidic condition, some of the endogenous interference factors can be excluded.

Experimental Design:
1. Preparation of the FARP Working Solution
(1) Prepare proper amount of FRAP working solution according to the samples numbers referring to the following table.

|  | 1 sample | 5 samples | 10 samples | 20 samples | 50 samples |
| --- | --- | --- | --- | --- | --- |
| TPTZ diluent | 150 μl | 750 μl | 1500 μl | 3000 μl | 7500 μl |
| TPPTZ solution | 15 μl | 75 μl | 150 μl | 300 μl | 750 μl |
|  | Mix thoroughly before adding the assay buffer | | | | |
| Assay buffer | 15 μl | 75 μl | 150 μl | 300 μl | 750 μl |
| FRAP working solution | 180 μl | 900 μl | 1800 μl | 3600 μl | 9000 μl |

The FRAP working solution was incubated at 37° C. and used no longer than 1-2 hours.

2. Preparation of Samples
Prepare 10 species of flavonoids: quercetin (Que), daidzein (Dai), kaempferol (Kae), apigenin (Api), naringenin (Nar), genistein (Gen), hesperidin (Her), luteolin (Lut), chrysin (Chr) and nobiletin (Nob). Make the final concentration of each flavonoid to 27 μM.

3. Preparation of Standard Curve:
Dissolve 27.8 mg of $FeSO_4 \cdot 7H_2O$ provided by this kit and dilute to 1 ml to make the concentration to 100 mM. Take an appropriate amount of $FeSO_4$ solution and dilute it to 0.15, 0.3, 0.6, 1.2 and 1.5 mM, respectively. Distilled water or sample preparation solution was used for the preparation of the standards. $FeSO_4$ solution must be freshly prepared when applied for assay.

4. Determination of Antioxidant Capacity:
(1) Add 180 μl FRAP working solution into each well of the 96-well plate;
(2) Adding 5 μl of distilled water or PBS or matched volume of assay buffer into the blank control wells. Add 5 μl $FeSO_4$ solution with different concentrations into the standard curve wells. Add 5 μl of different samples or 0.15 mM Trlox as a positive control. Then shake the plate gently.
(3) Incubate the plate at 37° C. for 3-5 min, and then determine the absorbance at 593 nm.

(4) Calculate the antioxidant capacity of the samples according to the standard curve.
(5) Representation of the antioxidant capacity: for the FRAP method, the antioxidant capacity is expressed using the $FeSO_4$ standard solution.

Figure 7:
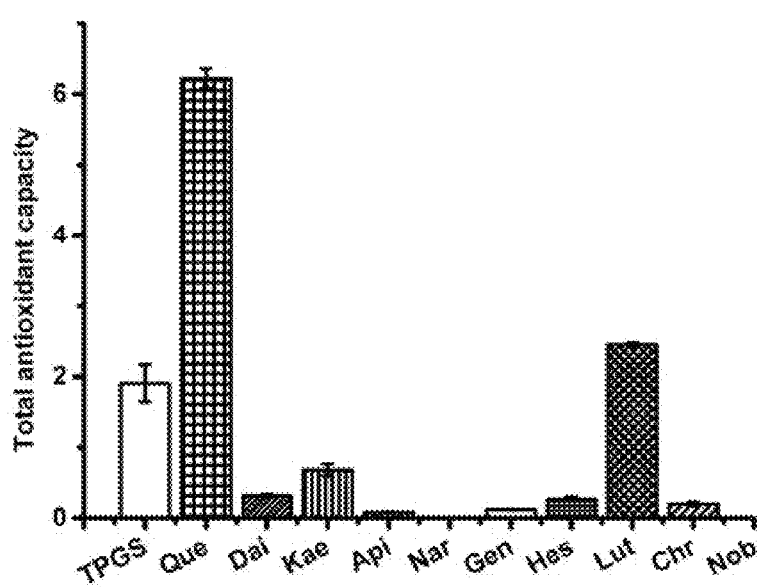
FIG. 7 Naringenin have little antioxidant activity and free radical scavenging capacity.

The results are shown in FIG. 7. The antioxidant capacity of naringenin is very weak, indicating that the effects of naringenin on sensitizing/synergizing tumor radiotherapy and ameliorating lung injury are not through its antioxidation capacity to scavenge the radiation-induced free radicals.

Finally, it should be noted that the abovementioned embodiments are only for those who skilled in the art to understand the essence of the present invention, and are not intended to limit the protection scope of the present invention.

The invention claimed is:

1. A method of sensitizing tumor radiotherapy as well as reducing radiation-induced toxicity, comprising the steps of:
   (1) administering orally an effective amount of medication before an irradiation;
   (2) conducting the irradiation;
   (3) administering orally the effective amount of the medication after the irradiation;
   wherein the medication comprises a small molecular flavonoid compound selected from the group consisting of naringenin, hesperetin, luteolin and apigenin.

2. The method according to claim 1, wherein the tumor radiotherapy is a clinically applicable radiation therapy method, consisting of:
   (1) external or internal radiation therapy;
   (2) stereotactic radiation therapy;
   (3) direct ionizing radiation therapy or indirect ionizing radiation therapy;
   (4) radiation therapy using X-ray therapy apparatus, medical accelerator or radioactive nuclide.

3. The method according to claim 1, wherein the tumor is a thoracic tumor.

4. The method according to claim 1, wherein the radiation-induced toxicity is tissue inflammation or tissue fibrosis caused by radiation.

5. The method according to claim 1, wherein the radiation-induced toxicity is radiation-induced lung injury consisting of radiation pneumonitis in the early stage of radiotherapy and radiation pulmonary fibrosis in the late stage of radiotherapy.

6. The method according to claim 1, wherein the small molecular flavonoid compound is naringenin or naringin.

7. The method according to claim 3, wherein the thoracic tumor is a lung tumor, an esophageal tumor, a breast tumor or a mediastinal tumor.

8. The method according to claim 1, wherein the tumor is a thoracic tumor.

9. The method according to claim 1, wherein the radiation-induced toxicity is tissue inflammation or tissue fibrosis caused by radiation.

10. The method according to claim 1, wherein the radiation-induced toxicity is radiation-induced lung injury including radiation pneumonitis in the early stage of radiotherapy and radiation pulmonary fibrosis in the late stage of radiotherapy.

* * * * *